(12) United States Patent
Guerra

(10) Patent No.: US 6,827,903 B2
(45) Date of Patent: Dec. 7, 2004

(54) INERT GAS FUSION ANALYZER

(75) Inventor: Carlos Guerra, Berring Springs, MI (US)

(73) Assignee: Leco Corporation, St. Joseph, MI (US)

( * ) Notice: Subject to any disclaimer, the term of this patent is extended or adjusted under 35 U.S.C. 154(b) by 360 days.

(21) Appl. No.: 10/035,716

(22) Filed: Oct. 26, 2001

(65) Prior Publication Data

US 2003/0082816 A1 May 1, 2003

(51) Int. Cl.$^7$ .................. G01N 21/00; G01N 27/00; G01N 31/00; G01N 33/00; G01N 7/00
(52) U.S. Cl. .................. 422/83; 422/50; 422/52; 422/68.1; 422/78; 422/81; 422/82.05; 422/91; 422/94; 422/95; 422/96; 422/97; 422/101; 436/43; 436/106; 436/127; 436/133; 436/134; 436/136; 436/139; 436/144; 436/149; 436/155; 436/164; 436/171; 436/172; 436/181; 73/1.01; 73/1.02; 73/23.2; 73/23.31; 356/51; 374/43; 374/44
(58) Field of Search ................. 422/50, 52, 68.1, 422/80, 78, 81, 82.05, 83, 91, 94, 95, 96, 97, 101; 436/43, 106, 127, 133, 134, 136, 139, 144, 149, 155, 164, 171, 172, 181; 73/1.01, 1.02, 23.2, 23.31; 356/51; 374/43, 44

(56) References Cited

U.S. PATENT DOCUMENTS

| | | | | |
|---|---|---|---|---|
| 3,660,036 A | * | 5/1972 | Benson | 436/57 |
| 4,329,868 A | * | 5/1982 | Kuznetsov et al. | 73/19.12 |
| 4,401,763 A | * | 8/1983 | Itoh | 436/115 |
| 4,573,910 A | * | 3/1986 | Bredeweg | 432/156 |
| 4,601,882 A | * | 7/1986 | Benner | 422/80 |
| 4,703,646 A | * | 11/1987 | Muller et al. | 73/24.01 |
| 5,473,162 A | * | 12/1995 | Busch et al. | 250/341.6 |
| 5,831,143 A | * | 11/1998 | Galloway et al. | 73/19.01 |
| 6,207,460 B1 | * | 3/2001 | Kishkovich et al. | 436/106 |
| 6,623,699 B1 | * | 9/2003 | Pack et al. | 422/80 |
| 6,627,155 B1 | * | 9/2003 | Uemura et al. | 422/83 |

OTHER PUBLICATIONS

Application No. 09/307,111, filed May 7, 1999, entitled Switched Mode NDIR System, specification and drawings.
Application No. 09/714,480 filed Nov. 15, 2000, entitled Analyzing System for High Accuracy Nitrogen, specification and drawings.
Application No. 09/772,021 filed Jan. 29, 2001, entitled Control Circuit for Thermal Conductivity Cell, specification and drawings.

* cited by examiner

Primary Examiner—Jill Warden
Assistant Examiner—Brian Sines
(74) Attorney, Agent, or Firm—Price, Heneveld, Cooper, Dewitt & Litton

(57) ABSTRACT

A single pass analyzer includes multiple infrared sensors, a catalytic converter, a scrubber and a thermal conductivity cell all coupled in series to provide a single pass (i.e., one sample) analyzer which allows for fast analysis, allows for the speciation of hydrogen samples, requires no purging between different sample types, utilizes a single carrier gas, and eliminates molecular sieves and Shutze converters. The resultant analyzer provides improved quicker results with less plumbing (i.e., gas conduits and valving) in a single instrument.

14 Claims, 7 Drawing Sheets

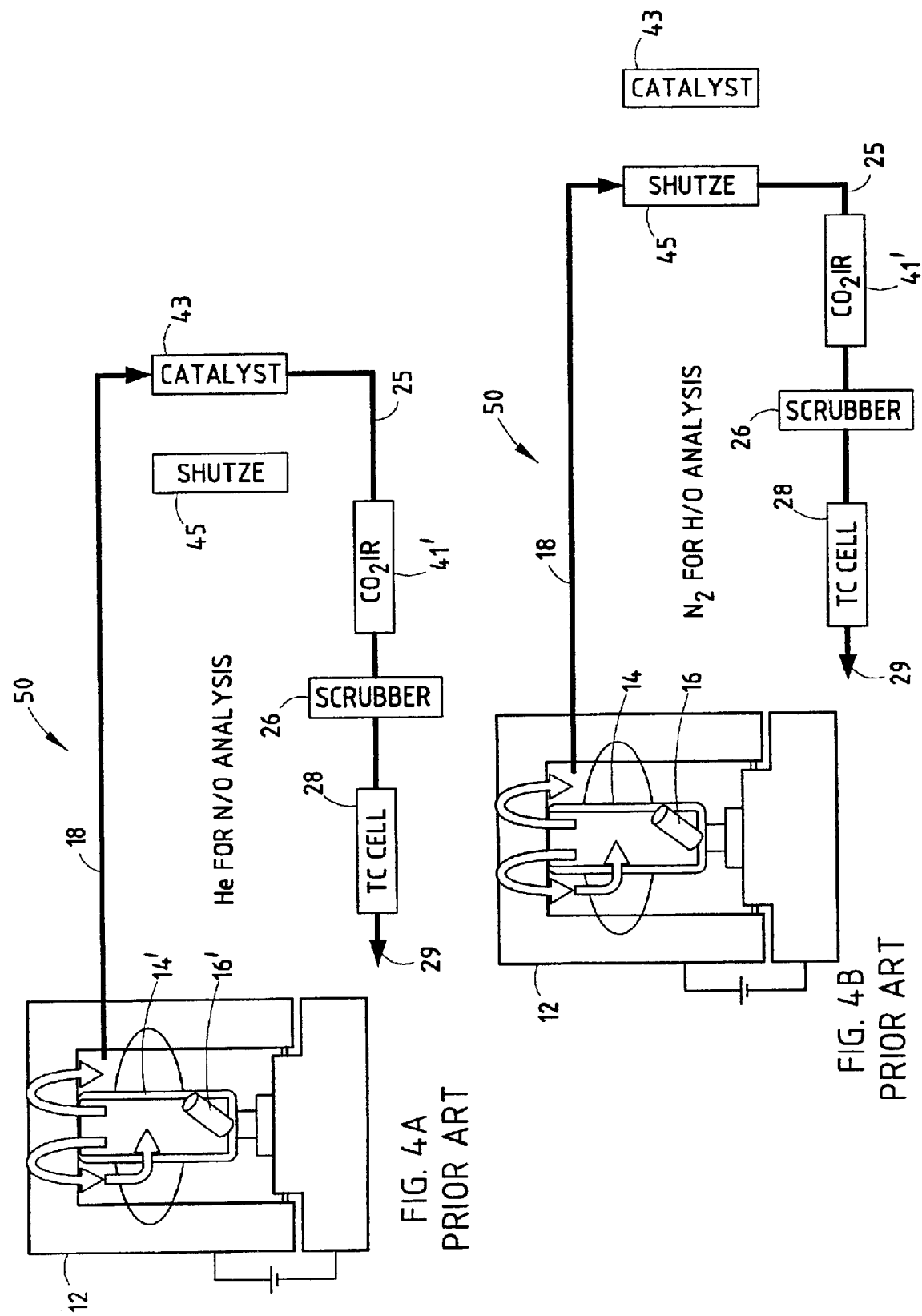

INERT GAS FUSION ANALYZER

BACKGROUND OF THE INVENTION

The present invention relates to analytical instruments and particularly to an inert gas fusion analyzer for simultaneously determining hydrogen, oxygen, and nitrogen.

In inert gas fusion instruments, it is typical to fuse a sample in an electrode furnace utilizing a carrier gas sweeping the byproducts of fusion through a variety of detectors, either infrared detectors or thermal conductivity cells, to determine the concentration of elements such as hydrogen, oxygen, and nitrogen. When thermal conductivity cells are employed, helium and hydrogen fall within one group of elements having particular thermal characteristics while nitrogen, argon, carbon dioxide, and water have significantly different thermal characteristics. As a result, in instruments employing thermal conductivity cells for the detection of elements, it is typical to use a carrier gas from one group, such as helium, to detect a specimen gas from another group, such as nitrogen or oxygen. Alternatively, when using thermal conductivity cells for detecting hydrogen, a heavier gas, such as nitrogen or argon, is employed so that the thermal conductivity cell can distinguish between the specimen gas and the carrier gas. As a result, the design of instruments for measuring hydrogen have resulted in a separate instrument from those instruments used to detect nitrogen and oxygen.

Although attempts have been made to, in effect, incorporate two instruments in one cabinet utilizing separate flow paths and requiring two separate samples to be run, there remains a need for a single path instrument which can measure hydrogen, oxygen, and nitrogen from a single sample and provide high accuracy for low concentration samples.

SUMMARY OF THE INVENTION

The present invention solves this need by the utilization of multiple infrared sensors, a catalytic converter, a scrubber and a thermal conductivity cell all coupled in a series flow path from an electrode furnace to provide a single pass (i.e., one sample) analyzer which allows for fast analysis, allows for the speciation of all analytes, including hydrogen samples, requires no purging of carrier gas between different sample types, utilizes a single carrier gas, and eliminates the molecular sieve chromatographic column and Shutze converters of prior art systems. The resultant analyzer, therefore, provides improved quicker results with less plumbing (i.e., gas conduits and valving) than prior art systems and does so in a single instrument.

These and other features, objects and advantages of the present invention will become apparent upon reading the following description thereof together with reference to the accompanying drawings.

BRIEF DESCRIPTION OF THE DRAWINGS

FIGS. 4A and 4B are flow diagrams for prior art nitrogen/oxygen and hydrogen analyzers;

DETAILED DESCRIPTION OF THE PREFERRED EMBODIMENT

Figure 1:
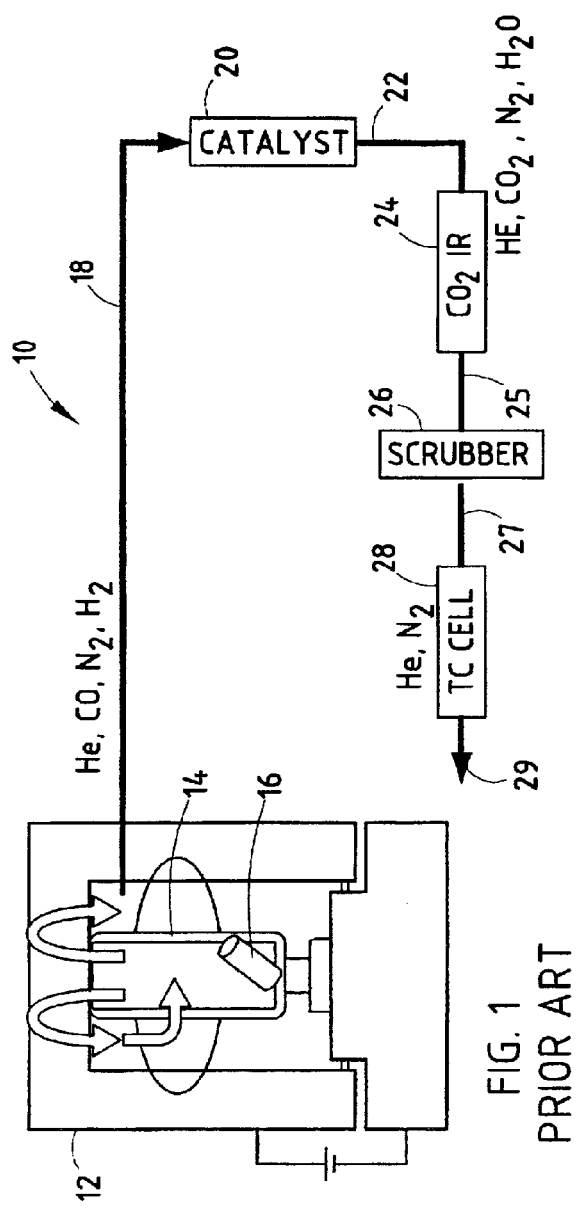
FIG. 1 is a flow diagram of a prior art nitrogen/oxygen analyzer.

Referring initially to FIG. 1, there is shown a prior art nitrogen/oxygen analyzer, such as a commercially available TC436 from Leco Corporation of St. Joseph, Mich. The analyzer 10 of FIG. 1 includes an impulse furnace 12 which can be incorporated in a single cabinet with the remaining elements of the analyzer. The furnace may be a type such as model EF400, also commercially available from Leco Corporation of St. Joseph, Mich. The furnace 12 includes a graphite crucible 14 for receiving a sample 16 which can be a pin sample, shavings, or take on any other form of sample typically being 1 gram and containing nitrogen and oxygen to be analyzed. The furnace includes a supply of carrier gas, such as helium, with the crucible being heated by the furnace to fuse the sample, and the resultant gaseous byproducts of fusion are swept through the analyzer by the helium carrier gas.

During fusion, the output flow path of the furnace includes conduit 18 leading the byproducts of fusion through a hot copper oxide catalyst 20 operating at a temperature of approximately 650° C., which converts byproducts of fusion, namely CO (carbon monoxide), to $CO_2$ (carbon dioxide) and $H_2$ (hydrogen) to $H_2O$ (water). The output conduit 22 of catalyst is coupled to a $CO_2$ infrared detector 24, which detects oxygen in the form of $CO_2$. The infrared detector can be of the type disclosed in U.S. patent application Ser. No. 09/307,111 filed May 7, 1999 and entitled Switched Mode NDIR System, now U.S. Pat. No. 6,326,620, the disclosure of which is incorporated herein by reference. The detector 24 provides an output signal to a microprocessor (not shown), which calculates the amount of oxygen in the sample in a known manner. Output conduit 25 from infrared detector 24 is coupled to a scrubber 26, which eliminates carbon dioxide and water from the flow of fusion byproducts, leaving only the carrier gas and nitrogen exiting through conduit 27, through thermal conductivity cell 28, and vented to the atmosphere at 29. The thermal conductivity cell can be of the type disclosed in U.S. patent application No. 09/772,021 filed Jan. 29, 2001, and entitled Control Circuit For Thermal Conductivity Cell, now U.S. Pat. No. 6,357,279, the disclosure of which is incorporated herein by reference, and detects the amount of nitrogen and provides an output signal to the microprocessor of the instrument. Suitable instrumentation, such as used in the commercially available TC500 instrument manufactured by Leco Corporation of St. Joseph, Mich., can be coupled to the infrared detector(s) and output of the thermal conductivity cell to provide an operator with a readout of the concentration of oxygen and nitrogen in a sample.

Figure 2:
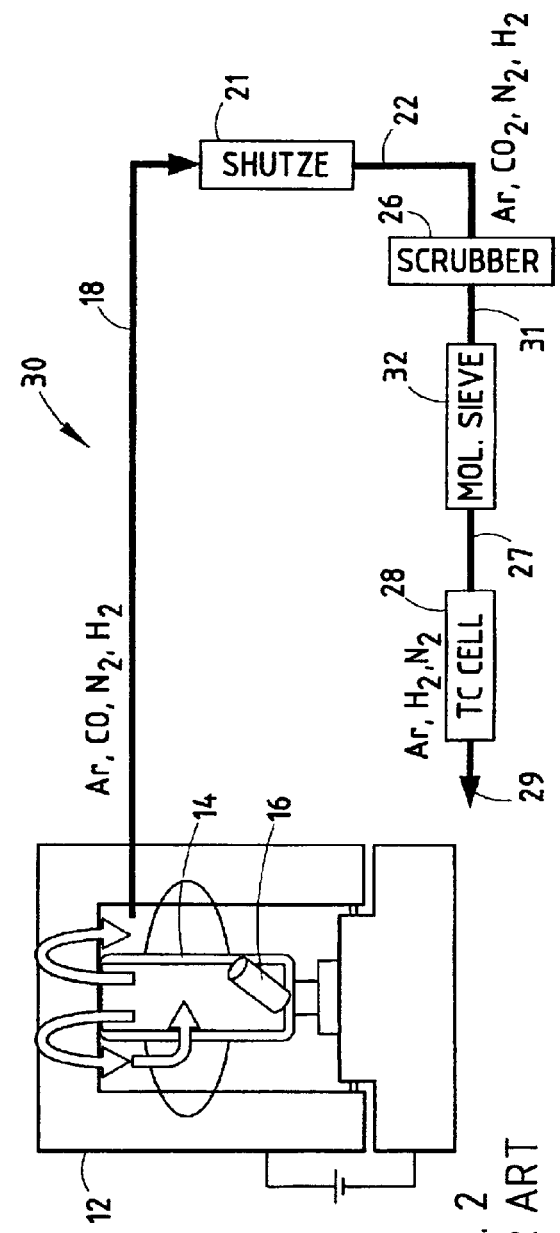
FIG. 2 is a flow diagram of a prior art hydrogen analyzer.

In order to detect hydrogen in a sample, however, a separate analyzer as shown in FIG. 2 has been employed, such as commercially available instrument model RH404 available from Leco Corporation of St. Joseph, Mich. In the analyzer 30 of FIG. 2, argon is employed as the carrier gas in view of the fact that the thermal conductivity cell employed to detect hydrogen cannot, as noted in the background of the invention, readily distinguish between helium and hydrogen, therefore, requiring the use of a carrier gas having different thermal characteristics than hydrogen. The analyzer 30 of FIG. 2 also includes a furnace 12 of the same type as FIG. 1 for fusing a sample 16 in a graphite crucible 14 and supplying the byproducts of fusion through an output conduit 18 to a Shutze converter 21, which operates at room temperature and employs iodine pentoxide ($I_2O_5$) to convert the carbon monoxide from fusion to carbon dioxide. These byproducts of fusion then are coupled by conduit 22 to a scrubber 26, which removes carbon dioxide from the flow path. The output 31 from scrubber 26 is applied to a molecular sieve 32, which separates the now nitrogen/hydrogen components of fusion in time spatial relationship with the hydrogen gas passing through the sieve first and being separated from the subsequent nitrogen peak. Conduit 27 couples the spatially separated gases to the thermal conductivity cell 28 for the detection of hydrogen. The carrier gas argon has no effect on the analysis since the thermal conductivity cell is normalized for such gas.

Although both the analyzers of FIGS. 1 and 2 provide accurate analyses for their respective gases of interest, they are separate analyzers requiring different carrier gases for the analysis of the three elements of interest.

Figures 3A, 3B:
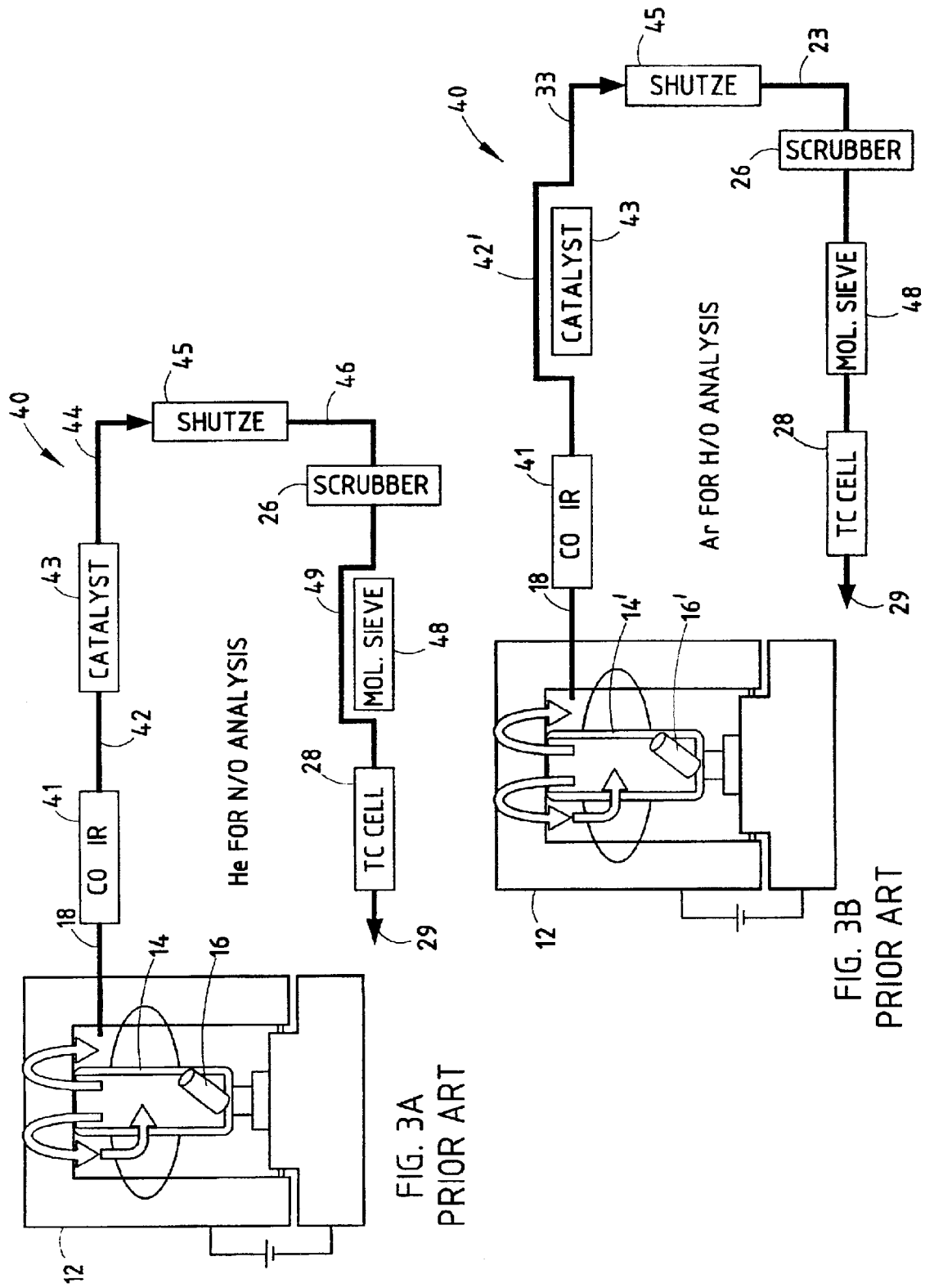
FIGS. 3A and 3B are flow diagrams for prior art nitrogen/oxygen and hydrogen analyzers.

Some efforts have been made to integrate two analyzers into a single cabinet which still requires the utilization of different carrier gases and two separate sample analyses to provide both nitrogen/oxygen and, separately, hydrogen analyses. FIGS. 3A and 3B illustrate one such analyzer 40 in which, in FIG. 3A, helium is employed as the carrier gas, while in the alternate flow path of FIG. 3B argon is used as the carrier gas. Analyzer 40 employs a furnace 12 as in the earlier embodiments to fuse a specimen 16 in a graphite crucible 14. The byproducts of fusion are supplied by conduit 18 in FIG. 3A to an infrared carbon monoxide detector 41 for detecting the oxygen content in a sample. Conduit 42 provides byproducts of fusion to a catalyst 43 which converts CO to $CO_2$ at 650° C. The output conduit 44 from catalyst 43 communicates with a Shutze converter 45 which has no effect on the helium carrier and the already converted carbon dioxide or other elements. Output 46 of converter 45 enters a scrubber 47 which removes carbon dioxide and water ($H_2O$).

Although a molecular sieve column 48 is in the analyzer, it is bypassed by suitable valving through conduit 49 such that the nitrogen is detected by a thermal conductivity cell 28 in this mode of operation. The byproducts are then exhausted through the atmosphere at 29. In FIG. 3A, therefore, a sample is fused, and it is assumed that most of the oxygen in this sample is converted to carbon monoxide, which is detected by detector 41 to provide an oxygen level measurement. The thermal conductivity cell 28 provides a nitrogen signal and hydrogen is not detected.

The same furnace 12 is employed as shown in FIG. 3B for fusing a separate sample 16' in another graphite crucible 14' to again provide byproducts of fusion through conduit 18 to the CO infrared detector 41 which detects the oxygen converted to carbon monoxide during fusion. In this configuration, the catalyst 43 is bypassed by a bypass conduit 42' by suitable valving such that the now argon carrier gas sweeps byproducts of fusion through the Shutze converter 45 which converts the carbon monoxide to carbon dioxide and to scrubber 26 which removes the carbon dioxide. In this configuration, the molecular sieve column 48 is in the flow path of byproducts of fusion, and bypass conduit 49 is blocked off by suitable valving such that hydrogen and nitrogen gases are separated by the molecular sieve to provide to thermal conductivity cell 28 a temporally resolved signal applied to a microprocessor (not shown) which outputs a signal representing the concentration of hydrogen. In order to operate the analyzer 40 in the two different modes represented by FIGS. 3A and 3B, it is necessary to purge the helium and byproducts of fusion from the analysis conducted under the flow path of FIG. 3A for from 4 hours to over night and subsequently run the second sample 16' with a different carrier, namely argon, to determine the amount of hydrogen in the sample. After an analysis run according to the flow path of FIG. 3B, it is again necessary to purge the system for 4 hours to over night to again run a nitrogen/oxygen sample, as shown in the FIG. 3A configuration. Also in this system, if hydrogen is released in any form other than $H_2$ gas, the hydrogen result will be biased since those gases have a different thermal conductivity than $H_2$ gas.

Another attempt has been made to combine in one physical cabinet, in effect, two analyzers for analyzing nitrogen and oxygen in one mode and hydrogen and oxygen in another mode, as represented by the analyzer 50 in FIGS. 4A and 4B. In FIGS. 4A and 4B again, a furnace 12 is employed for fusing a first sample 16 in a graphite crucible 14 and a second sample 16' in a second graphite crucible 14' (FIG. 4B) in the analyzer 50 shown in FIGS. 4A and 4B. The byproducts of fusion from furnace 12 are applied by conduit 18 to a valve selected parallel flow path comprising one of a Shutze converter and a high temperature catalytic converter 24. In the embodiment shown in FIG. 4A, helium is employed as the carrier gas, and the Shutze converter 45 is closed off from the flow path 18 by suitable valving (not shown) such that the byproducts of fusion flow through the catalyst 43, which converts hydrogen to water ($H_2O$) and CO to $CO_2$ at 650° C. An infrared $CO_2$ detector 41' is coupled by conduit 25 to the output of the catalytic converter 43 and detects oxygen in the form of carbon dioxide. A scrubber 26 removes the carbon dioxide and water from the gaseous byproducts of fusion and a thermal conductivity cell 28 detects the nitrogen in the sample. The thermal conductivity cell exhausts into the atmosphere at 29. Thus, in FIG. 4A, oxygen is detected by infrared cell 26 in the form of carbon dioxide and nitrogen is detected by thermal conductivity cell 28 with helium being employed as the carrier gas.

In order to employ the plumbing or flow path of the instrument 50 shown in FIGS. 4A and 4B for hydrogen, nitrogen is then employed as the carrier gas and, as seen in FIG. 4B, the catalyst 43 is bypassed by suitable valving forcing the byproducts of fusion to go through the Shutze converter 45, which converts carbon monoxide to carbon dioxide. The $CO_2$ infrared detector 41' detects oxygen in the form of $CO_2$. The gaseous flow stream then is passed through scrubber 26, which removes carbon dioxide, leaving the nitrogen (the carrier gas) and hydrogen flowing through the thermal conductivity cell 28 which, due to the different thermal conductivities of the two elements, can detect the difference between the hydrogen peak detected and the carrier gas to provide a hydrogen concentration signal to the microprocessor.

Again, as with the systems of 3A and 3B, it is necessary to purge the plumbing for from at least four hours to overnight when converting from helium as a carrier to nitrogen as a carrier and also necessary to run two separate analyses on two different samples. The extended purging time greatly delays the availability of results to the operator. Also with the systems shown in FIGS. 3A/B and 4A/B, significant additional valving and control circuits are necessary to switch from one mode to another when analyzing the two separate samples. Further, two different carrier gas supplies must also be employed. Also in this system, if hydrogen is released in any form other than $H_2$ gas (i.e., such as $CH_4$ or HCN), the hydrogen result will be biased since those gases have a different thermal conductivity than $H_2$ gas.

Figure 5:
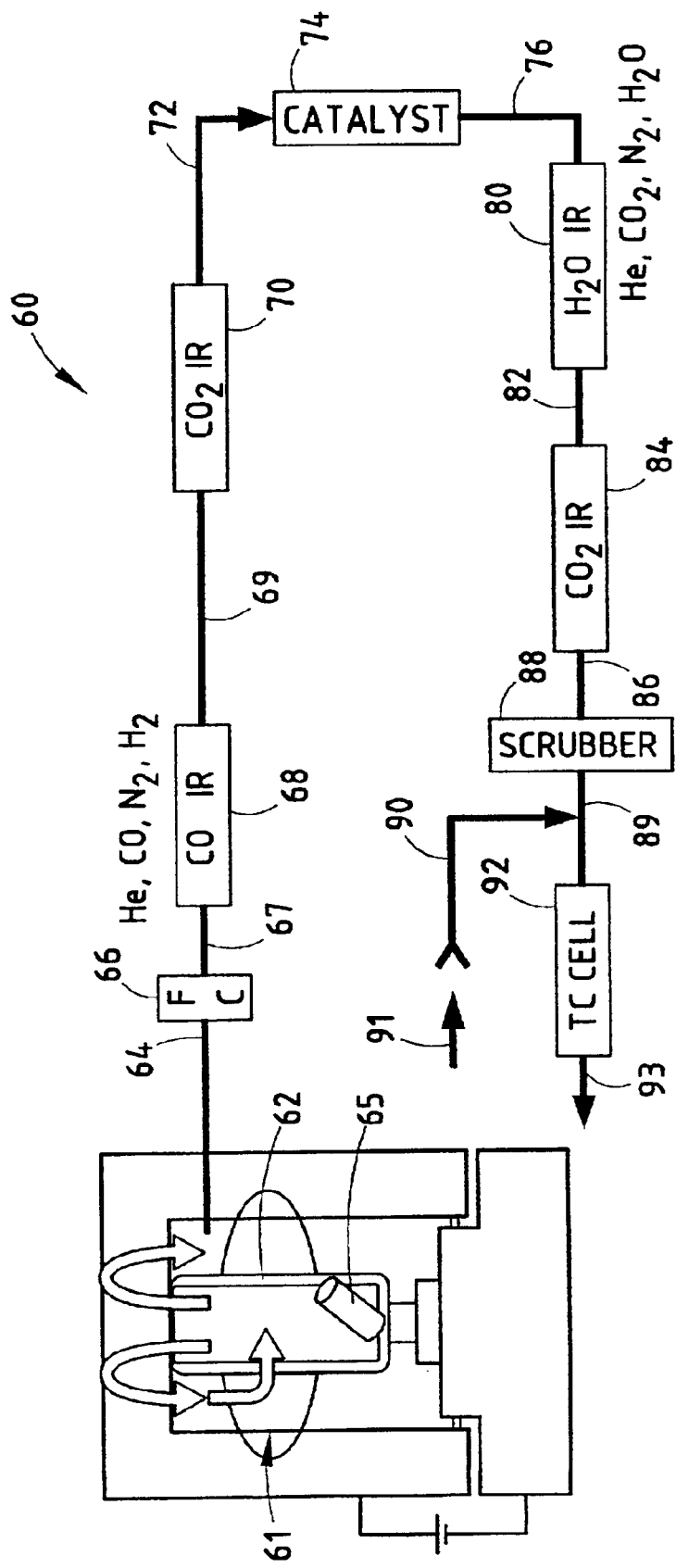
FIG. 5 is a flow diagram of the nitrogen/oxygen/hydrogen analyzer of the present invention.

The system of the present invention shown in FIG. 5 overcomes the difficulty of the prior art and allows detection of relatively low level concentrations of hydrogen and nitrogen in the presence of relatively high levels of oxygen in a truly single instrument with the ability to analyze in a single pass hydrogen, oxygen, and nitrogen. In FIG. 5, a single pass analyzer 60 is shown which employs an impulse furnace 61 for fusing a sample 65 in a graphite crucible 62 at approximately 2000° C.

The furnace 61 conventionally includes a disk filter, a micron filter, and flow controls to provide at output conduit 64 thereof a particle-free stream of byproducts of fusion from a sample 65, including carbon monoxide, carbon dioxide, hydrogen, nitrogen, in various molecular forms. Conduit 64 couples furnace 61 to a flow controller 66 which regulates the flow of gas through the system at 15 psi for the helium carrier employed at approximately 450 cc per minute. A first infrared detector 68 detects oxygen and is coupled by conduit 65 to flow controller 66. Inasmuch as a great deal of the oxygen in the sample is converted to carbon monoxide, detector 68 generally will detect and provide a measure of oxygen in relatively high concentrations of oxygen in a sample. Some of the oxygen reacts with the graphite crucible 65 to convert to carbon dioxide and the output of IR detector 68 is coupled by conduit 69 to a second IR detector 70 which detects carbon dioxide and provides a measurement of oxygen proportional to the amount of carbon dioxide in the specimen gas. As for relatively high concentrations of oxygen (i.e., above about 200 ppm) as explained below, the output of detectors 68 and 70 are summed to provide the total oxygen content of the sample. The sample flow path includes conduit 72 which is coupled to a conventional catalyst 74 which operates at about 650° C. and converts hydrogen to a gaseous form of $H_2O$ and converts any remaining carbon monoxide to carbon dioxide. Catalyst 74 may use copper oxide, rare earth copper oxide, or tungsten oxide as the catalytic agent.

Subsequently, conduit 76 couples the gaseous water vapor and the remaining byproducts of fusion to an $H_2O$ infrared detecting cell 80 which has a filter selected to detect $H_2O$ which is converted directly by catalyst 74 from the existing hydrogen in a sample. Cell 80 is mounted in the analyzer in a controlled environment holding its temperature at 50° C. Thus, the output signal of detector or cell 80 represents the amount of hydrogen in the sample. The output of detector 80 is coupled by conduit 82 to a second, high sensitivity $CO_2$ infrared sensor 84, which has the sensitivity to detect relatively low levels carbon dioxide (i.e., below about 200 ppm) and, therefore, oxygen in a sample.

Conduit 86 couples the flow of byproducts of fusion from infrared detector 84 to a scrubber 88 which removes $H_2O$ from the flow stream of helium carrier gas and remaining $CO_2$. A conduit 88 is coupled in a "T" to a conduit 90 to a carrier makeup stream 91 to maintain the pressure and flow rate of gas in conduits 86 and 89 substantially constant after scrubber 88 (which tends to reduce the pressure significantly). The carrier makeup conduit 90, its operation, and the flow path is described in greater detail in U.S. patent application Ser. No. 09/714,480 filed on Nov. 15, 2000, and entitled Analyzing System for High Accuracy Nitrogen Determination, now U.S. Pat. No. 6,623,699, the disclosure of which is incorporated herein by reference. Conduit 89 is coupled to thermal conductivity cell 92, which provides an output signal representative of the amount of nitrogen in a sample. Cell 92 can be of the type described in U.S. patent application Ser. No. 09/772,021 filed Jan. 29, 2001, and entitled Control Circuit for Thermal Conductivity Cell, now U.S. Pat. No. 6,357,279, the disclosure of which is incorporated herein by reference, and the output of which is vented to the atmosphere at 93.

With the system shown in FIG. 5, a single in series flow path is provided for the byproducts of fusion leaving furnace 61 and multiple infrared detectors are employed for measuring oxygen and hydrogen as water and a thermal conductivity cell is provided at the end of the flow stream for detecting nitrogen from the much different thermal characteristics of the helium carrier gas. The catalyst, scrubber, IR detectors, and TC cell can be of well known, conventional designs, although the IR detectors and TC cells of the preferred embodiment employ those disclosed in the above-identified patent applications. With the system of FIG. 5, therefore, a single analyzer is provided which can be employed for determining hydrogen, nitrogen, and oxygen in a single sample and which also has the ability to detect relatively high levels of hydrogen in a sample which normally would saturate detectors and/or with which carbon dioxide peaks would interfere.

Figure 8:
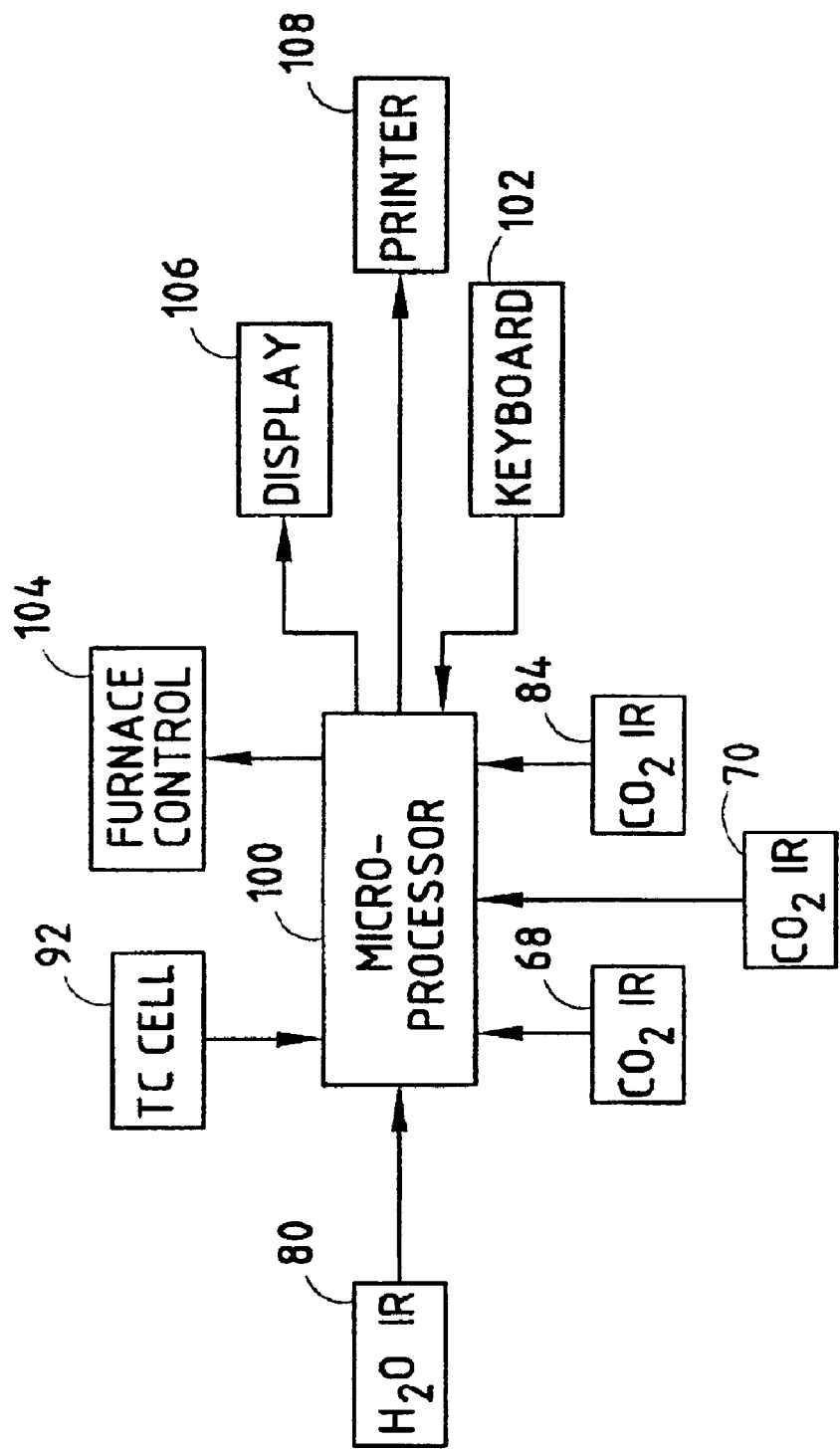
FIG. 8 is a block electrical circuit diagram of the analyzer of FIG. 5.

In order to prevent carbon dioxide interference, a lookup table is provided in the program for the microprocessor shown in FIG. 8, which compensates for carbon dioxide interference in the $H_2O$ IR detector 80. Once different known carbon dioxide levels have been detected, together with known concentrations of hydrogen, the amount of correction necessary to compensate the signal from detector 80 can be empirically determined and programmed into the memory to accommodate for carbon dioxide interference detected by the $H_2O$ detector 80. The correction factor so determined is then employed to provide an accurate hydrogen concentration for the output display of the analyzer.

Also, typically with $H_2O$ analysis, the water vapor can condense on the conduits of the system and cause tailing at cooler temperatures or as the system fouls. With the single flow path shown in the FIG. 5 circuit, no such fouling of the system was observed. In this embodiment, hydrogen travels through the flow system as $H_2$ gas, which has no affinity for cold spots or fouling. It is then converted to $H_2O$ immediately before it goes into detector 80. This is the reason the system of this invention does not show the typical problems associated with $H_2O$ analysis. Further, the system flow path shown in FIG. 5 allows for the analysis of samples with extremely high levels of hydrogen, which previously would have been thought to saturate detectors, such as thermal conductivity cells employed in the past.

Figure 6:
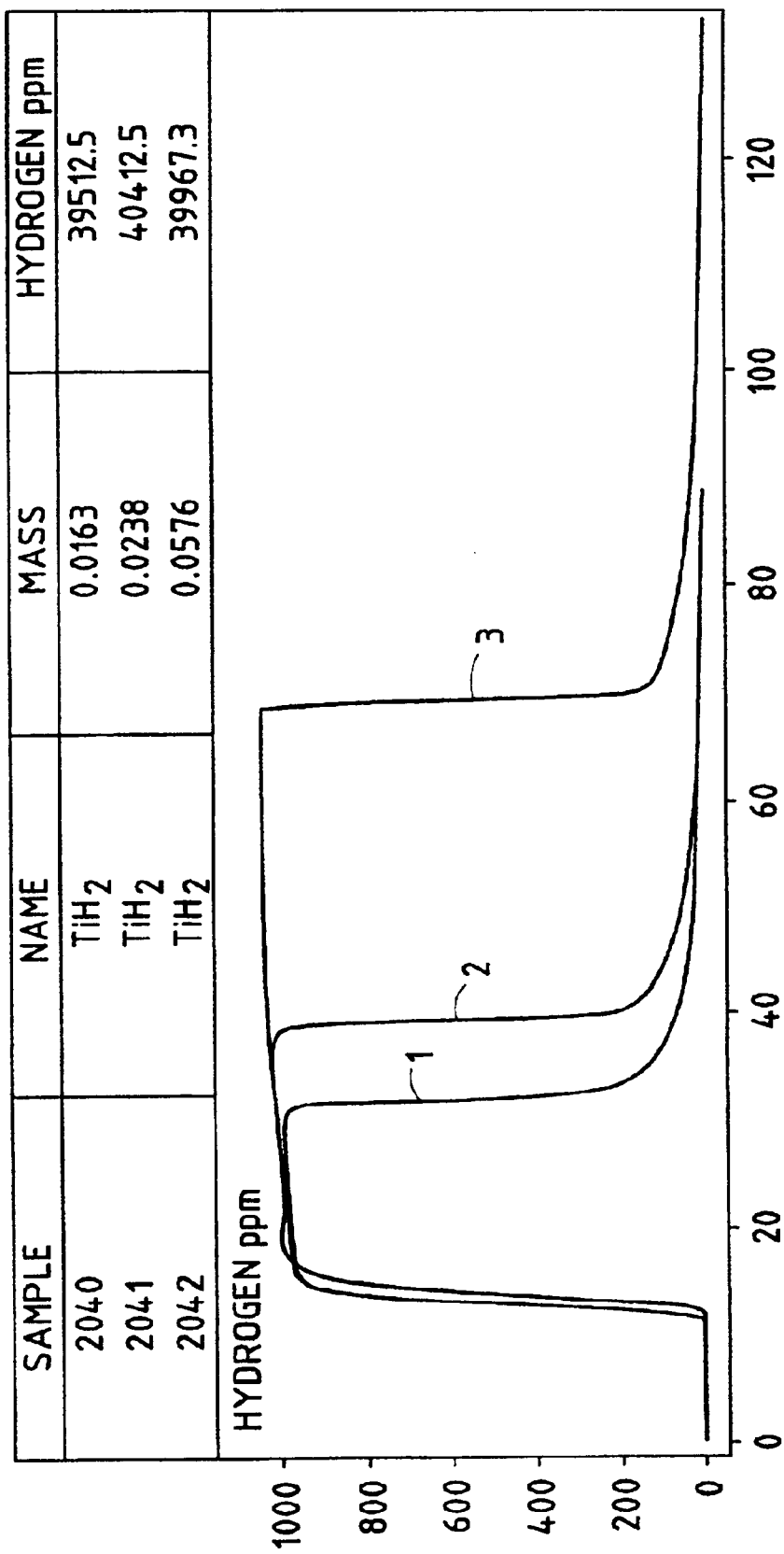
FIG. 6 is a graph showing the analysis of hydrogen in titanium hydride samples of three different masses.

FIG. 6 shows results of tests of pure samples of titanium hydride ($TiH_2$) for three samples having, as can be seen in the three curves shown in FIG. 6, a mass of 0.0163 grams for curve 1, 0.0238 grams for curve 2, and 0.0576 grams for curve 3. The measurement of the high amount of hydrogen (approximately 40,000 ppm) in each of the samples resulted in uniform measurement of the level of hydrogen. Further, in view of the sensitivity of the system shown in FIG. 5 to relatively low amounts of hydrogen and nitrogen in the presence of relatively high amounts of oxygen, significantly greater sensitivity of a sample containing such a mixture is provided.

Figure 7:
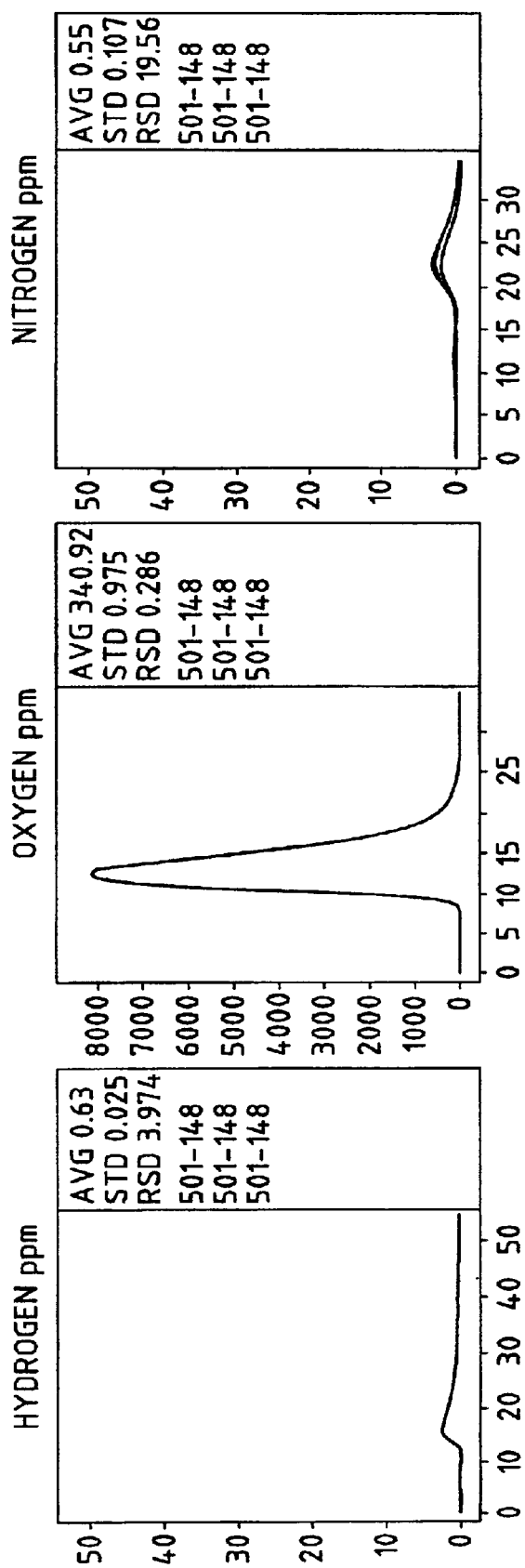
FIG. 7 is a graph showing the analysis results of samples of hydrogen, oxygen, and nitrogen for an analysis of a sample with relatively low concentrations of nitrogen and hydrogen and a high concentration of oxygen.

FIG. 7 shows graphs of hydrogen, oxygen, and nitrogen from tests done on multiple samples of the same material showing that hydrogen can be measured at a level of less than 0.63 ppm in the presence of oxygen having over 340 ppm, while nitrogen can also be measured at approximately 0.55 ppm in the same environment.

FIG. 8 shows a typical analyzer installation including electrical components coupled to the detectors and furnace shown in FIG. 5. In FIG. 8, a microprocessor 100 includes conventional input/output interfaces to receive signals from the thermal conductivity cell 92, the $H_2O$ infrared detector 80, the CO infrared detector 68, the high concentration $CO_2$ infrared detector 70, and the high sensitivity low $CO_2$ level detector 84. Operating instructions to initiate an analysis is provided by an operator through a keyboard 102, also coupled to the microprocessor, which has a signal output to a furnace control circuit 104 to operate furnace 61. A display 106, such as an LCD screen, is coupled to the output of microprocessor 100, as can be a printer 108 to provide printed results, such as shown in FIGS. 6 and 7.

The furnace control 104 can gradually ramp the temperature of a sample such that different compounds of the sample, including hydrogen compounds, can be released at different times, thereby not only identifying the total hydrogen content present in a sample but, by correlating the temperature at which the hydrogen compound is released, identifying the concentrations of certain hydrogen-bearing compounds themselves within the sample. As an example, the furnace 61 can be gradually increased in temperature from room ambient over a period of from 10 to 15 minutes to about 2000° C. At approximately 200° C., the hydrogen compound $H_2O$ will be released from the sample as a gaseous vapor. At about 300 to 500° C., hydrogen in gaseous form ($H_2$) will be released from the sample. Finally, above about 1000° C., the metal hydrides, such as $TiH_2$, will be released. These temperatures are reached over a period of time which can identify each of these compounds and others as they are detected by detector 80. The furnace control operates the furnace with increased current to ramp the temperature and operates at a maximum of about 6000 watts.

The system of FIG. 5 thereby provides a single instrument which can, with a single pass using a single carrier gas and a single sample, provide the information as to the total amount of hydrogen, oxygen, and nitrogen in a sample, as well as simultaneously speciating all analytes including hydrogen compounds, if desired, through the control of the furnace temperature, which greatly reduces the time to complete an N, O, H analysis and provides extremely high sensitivity to low levels of hydrogen and nitrogen either in the presence of either low or high levels of other analytes, such as oxygen. For bulk analysis, the analysis time for N, O, H is reduced to less than two minutes. Although He is employed as the carrier gas in the embodiment described, Ar could also be used.

It will become apparent to those skilled in the art that various modifications to the preferred embodiment of the invention as described herein can be made without departing from the spirit or scope of the invention as defined by the appended claims.

The invention claimed is:

1. A single pass analyzer for detecting the concentration of hydrogen, nitrogen, and oxygen in a sample comprising:
    a furnace for fusing a sample;
    a supply of carrier gas coupled to said furnace to provide an analyte stream of byproducts of fusion;
    conduits coupled to said furnace and to said supply for defining a conduit flow path for carrying byproducts of fusion in series through a plurality of detector and analyzer elements;
    a first infrared detector coupled in said conduit flow path for detecting oxygen in the form of CO in said sample;
    a second infrared detector coupled in said conduit flow path for detecting oxygen in the form of $CO_2$ in said sample;
    a catalyst coupled in said conduit flow path for converting hydrogen in hydrogen compounds to $H_2O$ and CO to $CO_2$;
    a third infrared detector having an input coupled to said catalyst for detecting hydrogen as $H_2O$ in the analyte stream from the catalyst;
    a fourth infrared detector comprising a high sensitivity $CO_2$ infrared detector coupled in said conduit flow path for detecting low levels of oxygen in the sample in the form of $CO_2$;
    a scrubber coupled to said fourth detector, said scrubber operative to remove $H_2O$ from the analyte stream; and
    a thermal conductivity cell coupled to said scrubber for detecting nitrogen in a sample.

2. The analyzer as defined in claim 1 wherein said catalyst is copper oxide operating at about 650° C.

3. The analyzer as defined in claim 2 and further including a flow controller coupled to said conduits.

4. The analyzer as defined in claim 3 and further including a supply of carrier makeup gas coupled between said scrubber and said thermal conductivity cell.

5. A single pass analyzer for detecting the concentration of hydrogen, nitrogen, and oxygen in a sample, said analyzer including a furnace for fusing a sample, and a supply of carrier gas for sweeping an analyte stream including the byproducts of fusion through a plurality of series-coupled elements comprising:
    a first infrared detector for detecting carbon monoxide from said sample;
    a second infrared detector coupled to said first infrared detector for detecting the carbon dioxide from said sample;
    a heated $C_uO$ catalyst coupled to said second infrared detector for converting hydrogen compounds to $H_2O$ and CO to $CO_2$;
    a third infrared detector coupled in series directly downstream of said catalyst for detecting hydrogen compounds as $H_2O$;
    a fourth infrared detector coupled to said third infrared detector for detecting oxygen in the form of $CO_2$;
    a scrubber coupled to said fourth infrared detector and operative to remove $H_2O$ from the analyte stream; and
    a thermal conductivity cell coupled to said scrubber for detecting nitrogen in the sample.

6. A method of determining the concentration of hydrogen in a sample in the form of different hydrogen compounds comprising:
    heating a specimen in a fusion furnace at temperatures increasing from room ambient to above about 1500° C.;
    sweeping the byproducts of fusion in an analyte stream from the furnace; and
    detecting the hydrogen compounds in the analyte stream as a function of temperature to identify concentrations of specific hydrogen compounds, wherein said detecting step includes employing a heated $C_uO$ catalyst to convert hydrogen compounds in the analyte stream to $H_2O$ and providing an $H_2O$ IR detector immediately downstream of the catalyst to detect hydrogen as a function of detected $H_2O$.

7. A method of determining the concentration of hydrogen in a sample in the form of different hydrogen compounds comprising:

heating a specimen in a fusion furnace at temperatures increasing from room ambient to above about 1500° C.;

sweeping the byproducts of fusion in an analyte stream from the furnace; and detecting the hydrogen compounds in the analyte stream as a function of temperature to identify concentrations of specific hydrogen compounds, wherein said compounds include $H_2O$, $H_2$, and metal hydrides.

8. The method as defined in claim 7 wherein said temperature is increased from room ambient temperature to about 2000° C.

9. A method of determining the concentration of hydrogen in a sample in the form of different hydrogen compounds comprising:

heating a specimen in a fusion furnace at temperatures increasing from room ambient to above about 1500° C.;

sweeping the byproducts of fusion in an analyte stream from the furnace;

detecting carbon dioxide levels in said analyte stream;

detecting the hydrogen compounds in the analyte stream as a function of temperature to identify concentrations of specific hydrogen compounds by employing a heated $C_uO$ catalyst to convert hydrogen compounds in the analyte stream to $H_2O$ and providing an $H_2O$ IR detector immediately downstream of the catalyst to detect hydrogen as a function of detected $H_2O$;

calculating the effect of detected $CO_2$ levels on the level of hydrogen measured by the $H_2O$ IR detector; and compensating the measured hydrogen level based upon the calculating step.

10. The method as defined in claim 9 wherein said compensating step is performed by a microprocessor using a look-up table of correction factors.

11. An analyzer for determining the concentration of hydrogen in a sample in the form of different hydrogen compounds comprising:

a fusion furnace for fusing a sample;

a crucible positioned in said furnace for holding a sample to be fused;

a supply of carrier gas coupled to said furnace for sweeping the byproducts of fusion in an analyte stream from the furnace;

a $C_uO$ catalyst coupled to said furnace to convert hydrogen compounds in the analyte stream to $H_2O$;

an $H_2O$ IR detector coupled to said catalyst immediately downstream of said catalyst to detect hydrogen as a function of detected $H_2O$; and a microprocessor coupled to said detector for calculating the effect of $CO_2$ on the level of hydrogen measured by the $H_2O$ IR detector and compensating the measured hydrogen level based upon the calculating step and further including a detector coupled to said furnace for detecting oxygen as carbon monoxide in said sample;

at least one infrared detector coupled to said furnace for detecting oxygen as carbon dioxide in said sample;

a scrubber coupled to said at least one infrared detector and operative to remove $H_2O$ from the analyte stream; and a thermal conductivity cell coupled to said scrubber for detecting nitrogen in the sample.

12. A single pass analyzer for determining the concentration of hydrogen, nitrogen, and oxygen in a sample comprising:

a furnace for fusing a sample;

a supply of carrier gas coupled to said furnace to provide an analyte stream of byproducts of fusion;

conduits coupled to said furnace and to said supply for defining a conduit flow path for carrying byproducts of fusion in series through a plurality of detector and analyzer elements;

a first infrared detector coupled in said conduit flow path for detecting oxygen in the form of CO in said sample;

a second infrared detector coupled in said conduit flow path for detecting oxygen in the form of $CO_2$ in said sample;

a catalyst coupled in said conduit flow path after said second infrared detector for converting hydrogen in hydrogen compounds to $H_2O$ and CO to $CO_2$;

a third infrared detector having an input coupled to said catalyst for detecting hydrogen as $H_2O$ in the analyte stream from the catalyst;

a fourth infrared detector comprising a high sensitivity $CO_2$ infrared detector coupled in said conduit flow path for detecting low levels of oxygen in the sample in the form of $CO_2$;

a scrubber coupled to said fourth detector, said scrubber operative to remove $H_2O$ from the analyte stream;

a thermal conductivity cell coupled to said scrubber for detecting nitrogen in a sample; and a microprocessor coupled to each of said detectors and to said thermal conductivity cell for simultaneously calculating the hydrogen, nitrogen, and oxygen concentrations in a sample.

13. The analyzer as defined in claim 12 and further including a display coupled to said microprocessor for displaying the calculated concentrations.

14. The analyzer defined in claim 13 further including a printer for printing the calculated concentrations.

* * * * *